US011518770B2

(12) United States Patent
Dai et al.

(10) Patent No.: US 11,518,770 B2
(45) Date of Patent: Dec. 6, 2022

(54) SESQUITERPENOID ANALOGS

(71) Applicant: Purdue Research Foundation, West Lafayette, IN (US)

(72) Inventors: Mingji Dai, West Lafayette, IN (US); Dexter Cameron Davis, West Lafayette, IN (US); Alexander Adibekian, Palm, FL (US); Dominic Gregor Hoch, Jupiter, FL (US); Zhong-Yin Zhang, West Lafayette, IN (US)

(73) Assignees: Purdue Research Foundation, West Lafayette, IN (US); University of Florida Research Foundation, Inc., Gainesville, FL (US)

(*) Notice: Subject to any disclaimer, the term of this patent is extended or adjusted under 35 U.S.C. 154(b) by 126 days.

(21) Appl. No.: 16/531,185

(22) Filed: Aug. 5, 2019

(65) Prior Publication Data
US 2020/0040000 A1 Feb. 6, 2020

Related U.S. Application Data

(60) Provisional application No. 62/746,126, filed on Oct. 16, 2018, provisional application No. 62/714,785, filed on Aug. 6, 2018.

(51) Int. Cl.
*C07D 493/10* (2006.01)

(52) U.S. Cl.
CPC .................... *C07D 493/10* (2013.01)

(58) Field of Classification Search
None
See application file for complete search history.

(56) References Cited

FOREIGN PATENT DOCUMENTS

CN 106957324 A 7/2017

OTHER PUBLICATIONS

Combs, Recent Advances in the Discovery of Competitive Protein Tyrosine Phosphatase 1B Inhibitors for the Treatment of Diabetes, Obesity, and Cancer, 2010, 53, pp. 2333-2344. (Year: 2010).*
Soderberg, http://chemwiki.ucdavis.edu/Organic_Chemistry/Organic_Chemistry_With_a_Biological_Emphasis/Chapter_13%3A_Reactions_with_stabilized_carbanion_intermediates_I/Section_13.1%3A_Tautomers (Year: 2019).*
PCT/US19/45044. International Search Report and Written Opinion of The International Search Authority. dated Oct. 28, 2019.
Dexter C. Davis, "Catalytic Carbonlylation in Total Synthesis and Chemistry and Biology of Aryl Isonitriles", A dissertation submitted to the Faculty of Purdue University in Partial Fulfillment pf the Requirements for the degree of Doctor of Philosophy, May 2017, pp. 1-216. Downloaded from: https//search.proquest.com p. 75, scheme 2.7.
Hu, C., et al., Rare Sesquiterpenoids from the Shed Trunk Barks of the Critically Endangered Plant Abies beshanzuensis and Their Bioactivities. European Journal of Organic Chemistry, 2016, issue 10, pp. 1832-1835.
Kang, Xian-Wen et al., Abiespiroside A, an Unprecedented Sesquiterpenoid Spirolactone with a 6/6/5 Ring System from Abies delavayi. Eur. J. Org. Chem. 2010, 6531-6534.
Hu, Chang-Ling et al., Rare Sesquiterpenoids from the Shed Trunk Barks of the Critically Endangered Plant Abies beshanzuensis and Their Bioactivities. Eur. J. Org. Chem. 2016, 1832-1835.

* cited by examiner

*Primary Examiner* — Savitha M Rao
*Assistant Examiner* — Andrew P Lee
(74) *Attorney, Agent, or Firm* — Purdue Research Foundation

(57) ABSTRACT

The present disclosure relates to novel sesquiterpenoid compounds as SHP2 and/or POLE3 inhibitors for potential treatment for cancers, and to methods of making and using the sesquiterpenoid compounds. The present invention therefore provides a method of using the disclosed compounds as chemosensitizations agent to a DNA damaging drugs for cancers.

6 Claims, No Drawings
Specification includes a Sequence Listing.

SESQUITERPENOID ANALOGS

CROSS-REFERENCE TO RELATED APPLICATION

This application claims the benefits of U.S. Provisional Application Ser. No. 62/714,785, filed Aug. 6, 2018, and 62/746,126, filed Oct. 16, 2018, the contents of which are incorporated herein entirely.

GOVERNMENT RIGHTS

This invention was made with government support under National Science Foundation Career Award No. 1553820 awarded by National Science Foundation, and National Institutes of Health Award No. P30CA023168 and RO1 CA207288 awarded by National Institutes of Health. The United States government has certain rights in the invention.

REFERENCE TO SEQUENCE LISTING

The present application incorporates by reference a file 68268-04_SEQ_ST25.txt including SEQ ID NO:1 to SEQ ID NO:4, provided in a computer readable form, created on Sep. 30, 2019 with a size of 2 KB, and filed with the present application. The sequence listing recorded in the file is identical to the written sequence listing provided herein.

TECHNICAL FIELD

The present disclosure relates to novel sesquiterpenoid compounds as SHP2 and/or POLE3 inhibitors for potential treatment for cancers, and to methods of making and using the sesquiterpenoid compounds.

BACKGROUND

This section introduces aspects that may help facilitate a better understanding of the disclosure. Accordingly, these statements are to be read in this light and are not to be understood as admissions about what is or is not prior art.

Natural products have always held a privileged position as valuable sources and inspirations for new drug development and often lead to the identification of new disease targets.

A family of *Abies* sesquiterpenoids represented by abiespiroside A, beshanzuenone C and beshanzuenone D have been reported. Abiespiroside A was isolated from the Chinese fir tree species *Abies delavayi* and was reported to possess potent inhibitory activity against the production of nitric oxide, a therapeutic effect for inflammatory diseases such as arthritis. Beshanzuenones C and D were isolated from the shed tree bark of the critically endangered Chinese fir tree species *Abies beshanzuensis*.

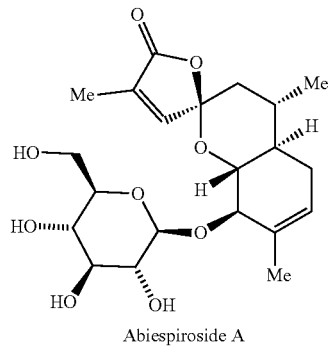

Abiespiroside A

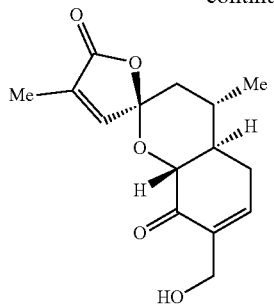

Beshanzuenone C

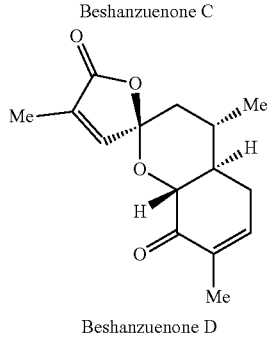

Beshanzuenone D

Both beshanzuenone C and D were reported to inhibit PTP1B, a key target for the treatment of type-II diabetes and obesity with $IC_{50}$ values of 59.7 and 40.4 µM, respectively. See Hu, C.-L., etc., *European Journal of Organic Chemistry* 2016, 10, 1832-1835.

Since rare and endangered plants have been shown to be superior sources for drug compounds compared to other botanical sources, it is possible that these natural products and/or their analogs may inhibit other additional cellular targets and therefore possess new biological activity for the treatment of other diseases.

SUMMARY

The present disclosure relates to novel sesquiterpenoid compounds as SHP2 and/or POLE3 inhibitors for potential treatment for cancers, and to methods of making and using the sesquiterpenoid compounds.

In one embodiment, the present disclosure provides compounds of formula I:

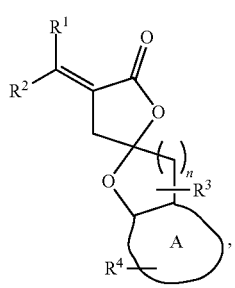

wherein
n is 1 or 2;
A is a $C_3$-$C_8$ saturated or unsaturated carbon ring;
$R^1$ and $R^2$ are each independently H, F, Cl, Br, optionally substituted $C_1$-$C_6$ straight or branched alkyl or alkenyl, optionally substituted aryl, or optionally substituted hetero aryl comprising one or more O, N, or S;

$R^3$ represents one or two optionally substituted $C_1$-$C_4$ straight or branched alkyl; and $R^4$ represents one or more H, —OH, carbonyl group, optionally substituted $C_1$-$C_4$ straight or branched alkyl, optionally substituted $C_1$-$C_4$ straight or branched alkoxy, optionally substituted aryl, or optionally substituted hetero aryl comprising one or more O, N, or S.

In one embodiment, the present disclosure provides a method of using compounds disclosed in the present disclosure as SHP2 inhibitors.

In one embodiment, the present disclosure provides a method of using compounds disclosed in the present disclosure as POLE3 inhibitors.

In one embodiment, the present disclosure provides a method of using compounds disclosed in the present disclosure as SHP2 and/or POLE3 inhibitors for cancer treatments.

DETAILED DESCRIPTION

For the purposes of promoting an understanding of the principles of the present disclosure, reference will now be made to the embodiments. It will nevertheless be understood that no limitation of the scope of this disclosure is thereby intended.

In the present disclosure the term "about" can allow for a degree of variability in a value or range, for example, within 10%, within 5%, or within 1% of a stated value or of a stated limit of a range.

In the present disclosure the term "substantially" can allow for a degree of variability in a value or range, for example, within 90%, within 95%, or within 99% of a stated value or of a stated limit of a range.

The term "substituted" as used herein refers to a functional group in which one or more hydrogen atoms contained therein are replaced by one or more non-hydrogen atoms. The term "functional group" or "substituent" as used herein refers to a group that can be or is substituted onto a molecule. Examples of substituents or functional groups include, but are not limited to, a halogen (e.g., F, Cl, Br, and I); an oxygen atom in groups such as hydroxyl groups, alkoxy groups, aryloxy groups, aralkyloxy groups, oxo (carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, azides, hydroxylamines, cyano, nitro groups, N-oxides, hydrazides, and enamines; and other heteroatoms in various other groups.

Non-limiting examples of substituents, that can be bonded to a substituted carbon (or other such as nitrogen) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, (CH$_2$)$_{0-2}$ P(O)OR$_2$, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$ N(R)C(O)R, (CH$_2$)$_{0-2}$N (R)C(O)OR, (CH$_2$)$_{0-2}$ N(R)N(R)$_2$, N(R)N(R)C(O)R, N(R) N(R)C(O)OR, N(R)N(R)CON(R)$_2$, N(R)SO$_2$R, N(R)SO$_2$N (R)$_2$, N(R)C(O)OR, N(R)C(O)R, N(R)C(S)R, N(R)C(O)N (R)$_2$, N(R)C(S)N(R)$_2$, N(COR)COR, N(OR)R, C(=NH)N (R)$_2$, C(O)N(OR)R, or C(=NOR)R wherein R can be hydrogen or a carbon-based moiety, and wherein the carbon-based moiety can itself be further substituted; for example, wherein R can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or R can be independently mono- or multi-substituted; or wherein two R groups bonded to a nitrogen atom or to adjacent nitrogen atoms can together with the nitrogen atom or atoms form a heterocyclyl, which can be mono- or independently multi-substituted.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons ($C_6$-$C_{14}$) or from 6 to 10 carbon atoms ($C_6$-$C_{10}$) in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

A heteroaryl ring is an embodiment of a heterocyclyl group. The phrase "heterocyclyl group" includes fused ring species including those that include fused aromatic and non-aromatic groups. Representative heterocyclyl groups include, but are not limited to pyrrolidinyl, azetidinyl, piperidynyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, tetrahydrofuranyl, pyrrolyl, oxazolyl, oxadiazolyl, imidazolyl, triazyolyl, tetrazolyl, benzoxazolinyl, benzthiazolinyl, and benzimidazolinyl groups.

The terms "halo," "halogen," or "halide" group, as used herein, by themselves or as part of another substituent, mean, unless otherwise stated, a fluorine, chlorine, bromine, or iodine atom. The compounds described herein may contain one or more chiral centers, or may, otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers find the like is also to be understood that such mixtures of stereoisomers may include a single stereochemical configuration t one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, aid compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

The term "optionally substituted," or "optional substituents," as used herein, means that the groups in question are either unsubstituted or substituted with one or more of the substituents specified. When the groups in question are substituted with more than one substituent, the substituents may be the same or different. When using the terms "independently," "independently are," and "independently selected from" mean that the groups in question may be the same or different. Certain of the herein defined terms may occur more than once in the structure, and upon such occurrence each term shall be defined independently of the other.

In one embodiment, the present disclosure provides compounds of formula I:

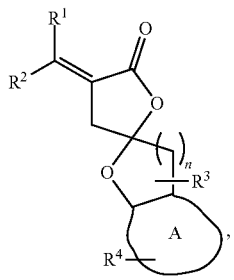

wherein
n is 1 or 2;
A is a $C_3$-$C_8$ saturated or unsaturated carbon ring;
$R^1$ and $R^2$ are each independently H, F, Cl, Br, optionally substituted $C_1$-$C_6$ straight or branched alkyl or alkenyl, optionally substituted aryl, or optionally substituted hetero aryl comprising one or more O, N, or S;
$R^3$ represents one or two optionally substituted $C_1$-$C_4$ straight or branched alkyl; and
$R^4$ represents one or more H, —OH, carbonyl group (=O), optionally substituted $C_1$-$C_4$ straight or branched alkyl, optionally substituted $C_1$-$C_4$ straight or branched alkoxy, optionally substituted aryl, or optionally substituted hetero aryl comprising one or more O, N, or S.

In one embodiment, the present disclosure provides compounds of formula I, wherein A is a $C_6$ saturated or unsaturated carbon ring. In one aspect, A is a $C_6$ unsaturated carbon ring.

In one embodiment, the present disclosure provides compounds of formula I, wherein $R^1$ and $R^2$ are each independently H, F, Cl, Br, $C_1$-$C_6$ straight or branched alkyl or alkenyl, an aryl selected from phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, or naphthyl; a hetero aryl selected from pyrrolidinyl, azetidinyl, piperidynyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, or tetrahydrofuranyl.

In one embodiment, the present disclosure provides compounds of formula I, wherein $R^1$ and $R^2$ are each independently H, F, Cl, Br, $C_1$-$C_6$ straight or branched alkyl.

In one embodiment, the present disclosure provides compounds of formula I, wherein $R^1$ and $R^2$ are each independently H.

In one embodiment, the present disclosure provides compounds of formula I, wherein n is 2.

In one embodiment, the present disclosure provides compounds of formula I, wherein one or more hydrogen on $R^1$ and/or $R^2$ may be optionally substituted by —OH, —F, —Cl, —Br, —CN, —NC, —$N_3$, or $C_1$-$C_4$ alkoxy.

In one embodiment, the present disclosure provides compounds of formula I, wherein $R^3$ represents one or two $C_1$-$C_4$ straight or branched alkyl, and one or more hydrogen on the $C_1$-$C_4$ straight or branched alkyl may be optionally substituted by one or more —OH, —F, —Cl, —Br, —CN, —NC, or —$N_3$, or $C_1$-$C_4$ alkoxy. In one aspect, $R^3$ is methyl group.

In one embodiment, the present disclosure provides compounds of formula I, wherein $R^4$ represents one or more substituting groups selected from the group of OH, carbonyl group, $C_1$-$C_4$ straight or branched alkyl, $C_1$-$C_4$ straight or branched alkoxy, or a combination thereof, wherein one or more H on the $C_1$-$C_4$ straight or branched alkyl and/or the $C_1$-$C_4$ straight or branched alkoxy is optionally substituted by one or more —OH, —F, —Cl, —Br, —CN, —NC, or —$N_3$.

In one embodiment, the present disclosure provides compounds of formula II,

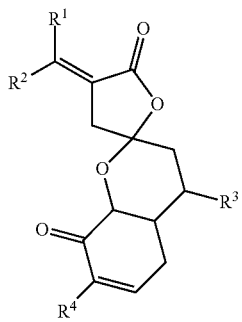

wherein either $R^1$-$R^4$ are all H, or at least one of $R^1$-$R^4$ is not H.

In one embodiment, the present disclosure provides compounds of formula II, wherein
$R^1$ and $R^2$ are each independently H, F, Cl, Br, optionally substituted $C_1$-$C_6$ straight or branched alkyl or alkenyl, optionally substituted aryl, or optionally substituted hetero aryl comprising one or more O, N, or S;
$R^3$ represents optionally substituted $C_1$-$C_4$ straight or branched alkyl; and
$R^4$ represents H, optionally substituted $C_1$-$C_4$ straight or branched alkyl, optionally substituted $C_1$-$C_4$ straight or branched alkoxy, optionally substituted aryl, or optionally substituted hetero aryl comprising one or more O, N, or S.

In one embodiment, the present disclosure provides compounds of formula II, wherein $R^1$ and $R^2$ are each independently H, F, Cl, Br, $C_1$-$C_6$ straight or branched alkyl or alkenyl, an aryl selected from phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, or naphthyl; a hetero aryl selected from pyrrolidinyl, azetidinyl, piperidynyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, or tetrahydrofuranyl.

In one embodiment, the present disclosure provides compounds of formula II, wherein $R^1$ and $R^2$ are each independently H, F, Cl, Br, $C_1$-$C_6$ straight or branched alkyl.

In one embodiment, the present disclosure provides compounds of formula II, wherein $R^1$ and $R^2$ are each independently H.

In one embodiment, the present disclosure provides compounds of formula II, wherein one or more hydrogen of $R^1$ and/or $R^2$ may be optionally substituted by —OH, —F, —Cl, —Br, —CN, —NC, —N$_3$, or $C_1$-$C_4$ alkoxy.

In one embodiment, the present disclosure provides compounds of formula II, wherein $R^1$ and $R^2$ are H.

In one embodiment, the present disclosure provides compounds of formula II, wherein $R^3$ represents $C_1$-$C_4$ straight or branched alkyl, and one or more hydrogen on the $C_1$-$C_4$ straight or branched alkyl may be optionally substituted by one or more —OH, —F, —Cl, —Br, —CN, —NC, or —N$_3$, or $C_1$-$C_4$ alkoxy. In one aspect, $R^3$ is methyl group.

In one embodiment, the present disclosure provides compounds of formula II, wherein $R^4$ represents $C_1$-$C_4$ straight or branched alkyl, or $C_1$-$C_4$ straight or branched alkoxy, wherein one or more H on the $C_1$-$C_4$ straight or branched alkyl or the $C_1$-$C_4$ straight or branched alkoxy is optionally substituted by —OH, —F, —Cl, —Br, —CN, —NC, or —N$_3$.

In one embodiment, the present disclosure provides compounds of formula III,

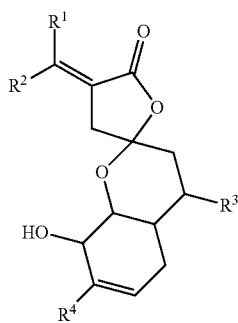

III wherein either $R^1$-$R^4$ are all H, or at least one of $R^1$-$R^4$ is not H.

In one embodiment, the present disclosure provides compounds of formula III, wherein
  $R^1$ and $R^2$ are each independently H, F, Cl, Br, optionally substituted $C_1$-$C_6$ straight or branched alkyl or alkenyl, optionally substituted aryl, or optionally substituted hetero aryl comprising one or more O, N, or S;
  $R^3$ represents optionally substituted $C_1$-$C_4$ straight or branched alkyl; and
  $R^4$ represents H, optionally substituted $C_1$-$C_4$ straight or branched alkyl, optionally substituted $C_1$-$C_4$ straight or branched alkoxy, optionally substituted aryl, or optionally substituted hetero aryl comprising one or more O, N, or S.

In one embodiment, the present disclosure provides compounds of formula III, wherein $R^1$ and $R^2$ are each independently H, F, Cl, Br, $C_1$-$C_6$ straight or branched alkyl or alkenyl, an aryl selected from phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, or naphthyl; a hetero aryl selected from pyrrolidinyl, azetidinyl, piperidynyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, or tetrahydrofuranyl.

In one embodiment, the present disclosure provides compounds of formula III, wherein $R^1$ and $R^2$ are each independently H, F, Cl, Br, $C_1$-$C_6$ straight or branched alkyl.

In one embodiment, the present disclosure provides compounds of formula III, wherein $R^1$ and $R^2$ are each independently H.

In one embodiment, the present disclosure provides compounds of formula III, wherein one or more hydrogen of $R^1$ and/or $R^2$ may be optionally substituted by —OH, —F, —Cl, —Br, —CN, —NC, —N$_3$, or $C_1$-$C_4$ alkoxy.

In one embodiment, the present disclosure provides compounds of formula III, wherein $R^3$ represents $C_1$-$C_4$ straight or branched alkyl, and one or more hydrogen on the $C_1$-$C_4$ straight or branched alkyl may be optionally substituted by one or more —OH, —F, —Cl, —Br, —CN, —NC, or —N$_3$, or $C_1$-$C_4$ alkoxy. In one aspect, $R^3$ is methyl group.

In one embodiment, the present disclosure provides compounds of formula III, wherein $R^4$ represents $C_1$-$C_4$ straight or branched alkyl, or $C_1$-$C_4$ straight or branched alkoxy, wherein one or more H on the $C_1$-$C_4$ straight or branched alkyl or the $C_1$-$C_4$ straight or branched alkoxy is optionally substituted by —OH, —F, —Cl, —Br, —CN, —NC, or —N$_3$ In one embodiment, the present disclosure provides compounds of formula I, II or III, wherein the compounds are selected from the group consisting of:

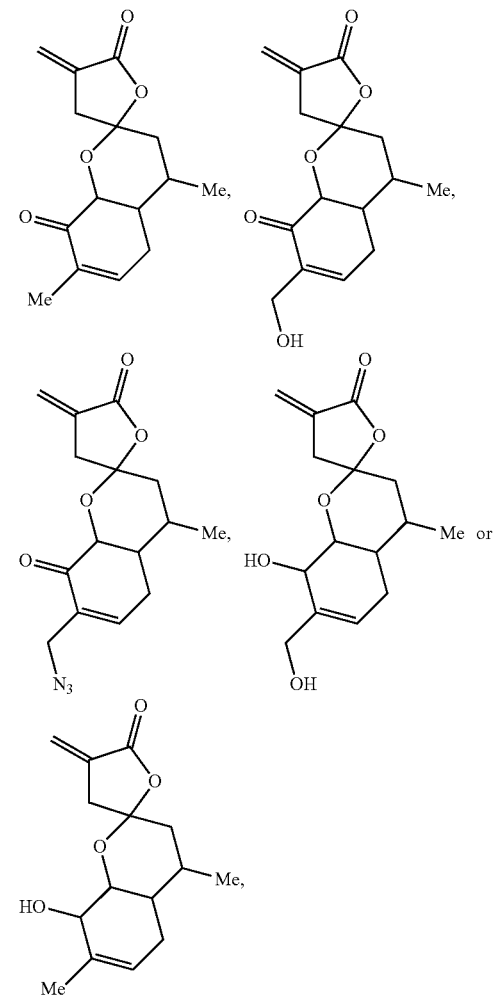

or any stereoisomer such as an enantiomer or diastereomer, or a combination thereof.

In one embodiment, the present disclosure provides compounds of formula I, II or III, wherein the compounds are selected from the group consisting of:

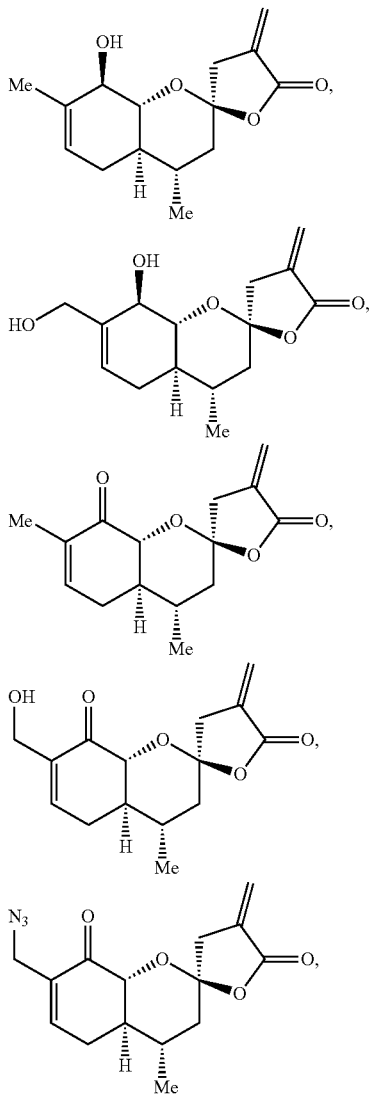

and any combination thereof.

In any embodiment, compounds of formula I, II, or III may be any stereoisomer such as an enantiomer or diastereomer, or a combination thereof.

In one embodiment, the present invention provides a compound of Formula I and/or and/or III as an SHP2 inhibitor.

In one embodiment, the present invention provides a compound of Formula I and/or II, and/or III as a POLE3 inhibitor.

In one embodiment, the present invention provides a compound of Formula I and/or II, and/or III as SHP2 and/or POLE3 inhibitors for cancer treatments.

In one embodiment, the present invention provides a method of using a compound of Formula I and/or II, and/or III as a chemosensitization agent to a DNA damaging drugs for cancer. In one aspect, the DNA damaging drug for cancer is etoposide.

Experiments

Reactions were performed using standard syringe techniques under argon unless stated otherwise. Starting materials and reagents were used as received from suppliers (Aldrich, Alfa Aeser, Acros.) Anhydrous THF was distilled over sodium benzophenone under argon. Acetonitrile ($CH_3CN$), dichloromethane ($CH_2Cl_2$), methanol (MeOH) and toluene were purified by passing the previously degassed solvents through activated alumina columns. Flash chromatography was performed using silica gel (230-400 mesh). Thin layer chromatography (TLC) was performed using glass-backed silica plates (Silicycle). NMR spectra were recorded on a Bruker ARX-400 spectrometer or AV-500 spectrometer at room temperature. Chemical shifts (in ppm) are given in reference to the solvent signal [$^1$H NMR: $CDCl_3$ (7.26); $^{13}$C NMR: $CDCl_3$ (77.2)]. $^1$H NMR data are reported as follows: chemical shifts (δ ppm), multiplicity (s=singlet, d=doublet, t=triplet, q=quartet, quin=quintuplet, m=multiplet, br=broad), coupling constant (Hz), and integration. $^{13}$C NMR data are reported in terms of chemical shift and multiplicity. IR data were recorded on a Thermo Nicolet Nexus 470 FTIR. High-resolution mass measurements for compound characterization were carried out using a FinniganMAT XL95 double focusing mass spectrometer system.

Preparation 1: (1R,2R,6R)-3-methyl-6-(prop-1-en-2-yl)cyclohex-3-ene-1,2-diol

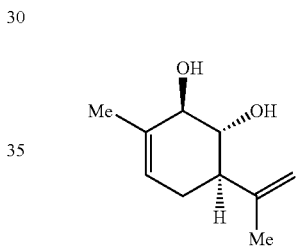

The synthesis of Preparation 1 is illustrated with Scheme 1:

Scheme 1: Synthesis of Preparation 1

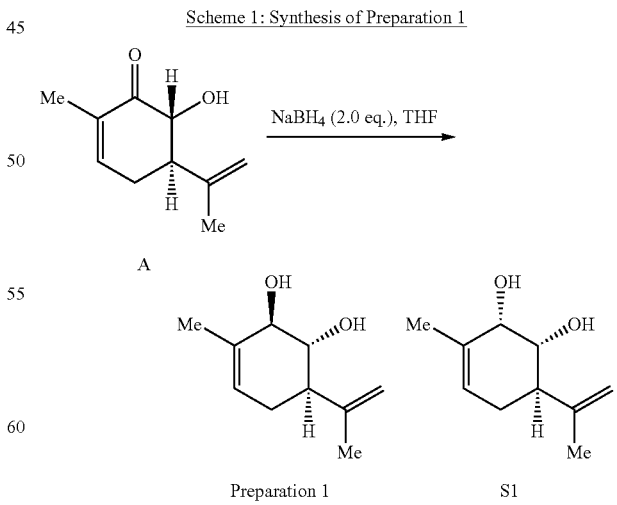

To a solution of compound A (15.0 g, 90.2 mmol, prepared in 48% yield over 3 steps from (+)-carvone as described by Dos Santos et al., see Dos Santos, R. B.;

Brocksom, T. J.; Zanotto, P. R.; Brocksom, U. *Molecules*, 2002, 7, 129-134) in THF (450 mL) was added sodium borohydride (6.83 g, 180.5 mmol) at room temperature and the resulting solution was stirred for 3 h. Water (200 mL) and ethyl acetate (200 mL) were added and the aqueous phase was extracted three times with ethyl acetate (3×100 mL.) The combined organic phases were washed with brine (200 mL), dried over sodium sulfate, filtered and concentrated under reduced pressure. The resulting residue was purified by flash chromatography (hexanes:ethyl acetate 2:1) to yield the desired preparation 1 as a white solid (13.1 g, 80%) and side product S1 as a colorless oil (2.63 g, 16%). Spectral data matched that reported by Koo et al. See Kim, H. J.; Su, L.; Jung, H.; Koo, S. *Org. Lett.* 2011, 13, 2682-2685.

Preparation 2: (4S,4 aR,8R,8aR)-8-hydroxy-4,7-dimethyl-3,4,4 a,5,8,8a-hexahydro-2H-chromen-2-one

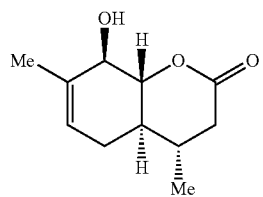

The synthesis of Preparation 2 is illustrated with Scheme 2.

Scheme 2: Synthesis of Preparation 2

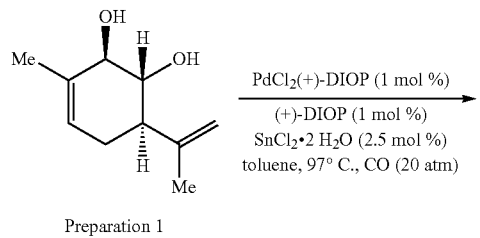

Preparation 1

PdCl$_2$(+)-DIOP (1 mol %)
(+)-DIOP (1 mol %)
SnCl$_2$·2 H$_2$O (2.5 mol %)
toluene, 97° C., CO (20 atm)

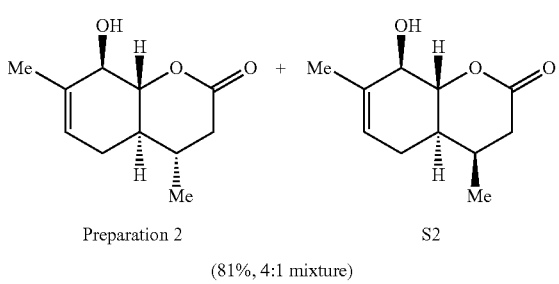

Preparation 2         S2

(81%, 4:1 mixture)

Preparation 3: (4S,4aR,8R,8aR)-8-((tert-butyldimethylsilyl)oxy)-4,7-dimethyl-3,4,4a,5,8,8a-hexahydro-2H-chromen-2-one

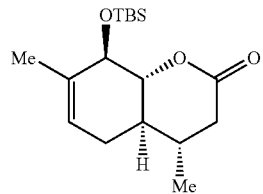 [SMILES: CC1=CC[C@H]2[C@@H](OC(=O)C[C@@H]2C)[C@@H]1O[Si](C)(C)C(C)(C)C]

The synthesis of Preparation 3 is illustrated with Scheme 3:

Scheme 3: Synthesis of Preparation 3

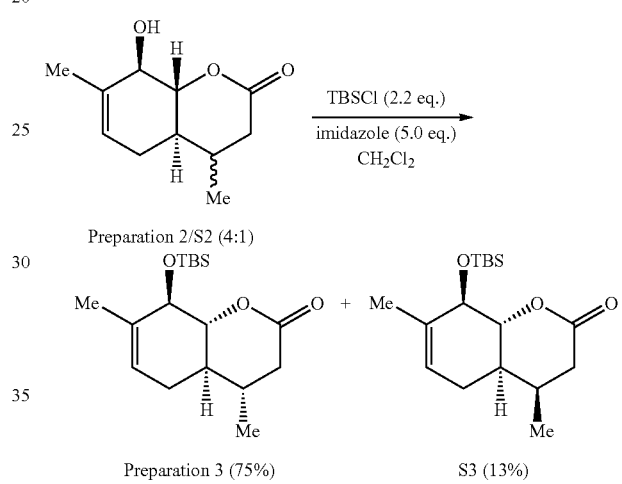

Preparation 2/S2 (4:1)

Preparation 3 (75%)         S3 (13%)

To a stirred solution of a mixture of Preparation 2/S2 (7.20 g, 36.69 mmol, 4:1 mixture) and imidazole (12.49 g, 183.4 mmol) in CH$_2$Cl$_2$ (183 mL) was added tert-butyldimethylsilyl chloride (12.17 g, 80.72 mmol) in portions at 0° C. The resulting solution was warmed to room temperature and stirred for 16 h. Water (50 mL) was added and the aqueous phase was extracted with CH$_2$Cl$_2$ (3×20 mL.) The combined organic phases were washed with brine (50 mL), dried over sodium sulfate, filtered and concentrated under reduced pressure. The resulting yellow solid was purified by flash chromatography (hexanes:ethyl acetate 20:1) to yield 14 as a white solid (8.54 g, 75%.) and S2 as a white solid (1.48 g, 13%). Preparation 3 (less polar isomer): $^1$H NMR (500 MHz, CDCl$_3$) δ 5.41 (dq, J=5.4, 1.7 Hz, 1H), 4.21-4.10 (m, 1H), 4.01 (dd, J=11.6, 7.6 Hz, 1H), 2.67 (dd, J=17.7, 5.9 Hz, 1H), 2.38-2.19 (m, 1H), 2.11 (dd, J=17.7, 10.6 Hz, 1H), 1.84-1.73 (m, 2H), 1.70 (s, 3H), 1.44 (qd, J=10.8, 5.2 Hz, 1H), 0.96 (d, J=6.5 Hz, 3H), 0.90 (s, 9H), 0.21 (s, 3H), 0.13 (s, 3H). $^{13}$C NMR (125 MHz, CDCl$_3$) δ 170.2, 135.9, 121.8, 86.3, 75.1, 40.0, 38.1, 32.0, 28.9, 26.2 (3 C), 20.0, 18.9, 18.6, −3.6, −4.6. IR (neat, cm$^{-1}$): 2952, 2928, 2857, 1717, 1381, 1248, 1074. HRMS (ESI): m/z=311.2042 calc. for C$_{17}$H$_{31}$O$_3$Si[M+H]$^+$, found 311.2040. Compound S3 (more polar isomer): $^1$H NMR (500 MHz, CDCl$_3$) δ 5.47-5.43 (m, 1H), 4.29-4.08 (m, 2H), 2.60 (dd, J=5.7 Hz, 1H), 2.45 (dd, J=17.3, 3.1 Hz, 1H), 2.13-1.91 (m, 4H), 1.72 (s, 3H), 1.02 (d, J=7.1 Hz, 3H), 0.93 (s, 9H), 0.24 (s, 3H), 0.15 (s, 3H). $^{13}$C NMR (125 MHz, CDCl$_3$) δ 170.4, 135.7, 122.4, 82.5, 76.1, 39.0, 37.1, 28.5, 27.7, 26.3 (3 C), 20.1, 18.7, 14.4, −3.5, −4.6. IR (neat, cm$^{-1}$) 2955, 2929, 2856, 1732, 1472, 1249, 1061. HRMS (ESI): m/z=311.2042 calc. for C$_{17}$H$_{31}$O$_3$Si[M+H]$^+$, found 311.2040.

Preparation 4: (2R,4S,4aR,8R,8aR)-8-((tert-butyldimethylsilyl)oxy)-4,7-dimethyl-4'-methylene-3,3',4,4a,4',5,8,8a-octahydro-5'H-spiro[chromene-2,2'-furan]-5'-one

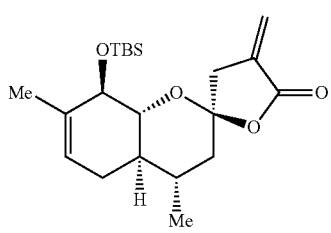 [SMILES: C=C1C[C@@]2(C[C@H](C)[C@H]3CC=C(C)[C@@H](O[Si](C)(C)C(C)(C)C)[C@@H]3O2)OC1=O]

The synthesis of Preparation 4 is illustrated with Scheme 4:

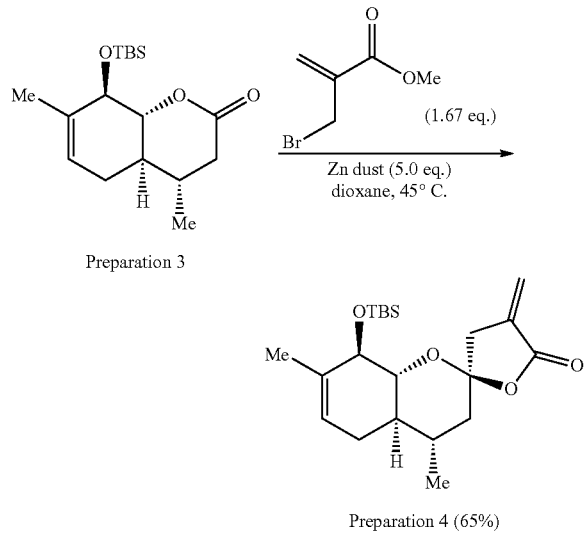

To a stirred solution of Preparation 3 (4.38 g, 14.1 mmol) and activated zinc dust (4.61 g, 70.5 mmol) in dioxane (14 mL) heated to 45° C. was added a solution of methyl 2-(bromomethyl)acrylate (4.22 g, 23.6 mmol, prepared as described by Ryu et al. See Kippo, T.; Fukuyama, T.; Ryu, I. *Org. Lett.* 2011, 13, 3864-3867.) in dioxane (14 mL). The mixture was stirred at the same temperature for 16 h, then 2 N HCl (20 mL) and ethyl acetate (20 mL) were added. The aqueous phase was extracted three times with ethyl acetate (10 mL) and the combined organic layers dried over sodium sulfate, filtered, and concentrated under reduced pressure. The resulting residue was purified by flash chromatography (hexanes:ethyl acetate 20:1) to yield Preparation 4 as a white solid (3.48 g, 65%.) $^1$H NMR (500 MHz, CDCl$_3$) δ 6.25 (dd, J=3.2, 2.4 Hz, 1H), 5.68-5.57 (m, 1H), 5.40 (dq, J=5.1, 1.6 Hz, 1H), 4.04 (dq, J=7.6, 1.6 Hz, 1H), 3.79 (dd, J=11.4, 7.5 Hz, 1H), 2.96 (dt, J=17.3, 2.3 Hz, 1H), 2.81 (dt, J=17.3, 3.0 Hz, 1H), 2.33-2.15 (m, 1H), 1.95-1.79 (m, 2H), 1.72 (ddq, J=11.8, 5.9, 2.9 Hz, 1H), 1.67 (s, 3H), 1.54-1.40 (m, 1H), 1.29-1.17 (m, 1H), 0.91 (d, J=6.3 Hz, 3H), 0.84 (s, 9H), 0.05 (s, 3H), 0.00 (s, 3H).$^{13}$C NMR (125 MHz, CDCl$_3$) δ 169.1, 135.8, 134.8, 122.7, 122.2, 105.0, 79.5, 74.9, 43.0, 41.4, 40.9, 30.7, 28.6, 26.2 (3 C), 20.4, 18.7, 18.5, −3.6, −4.2. IR (neat, cm$^{-1}$): 2949, 2929, 2882, 2857, 1768, 1250, 1123, 961, 838. HRMS (ESI): m/z=379.2305 calc. for C$_{21}$H$_{34}$O$_4$Si [M+H]$^+$, found 379.2302.

EXAMPLES

Example 1: (2R,4S,4aR,8R,8aR)-8-hydroxy-4,7-dimethyl-4'-methylene-3,3',4,4a,4',5,8,8a-octahydro-5'H-spiro[chromene-2,2'-furan]-5'-one

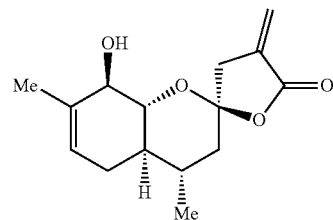 [SMILES: C=C1C[C@@]2(C[C@H](C)[C@H]3CC=C(C)[C@@H](O)[C@@H]3O2)OC1=O]

The synthesis of Example 1 is illustrated with Scheme 5:

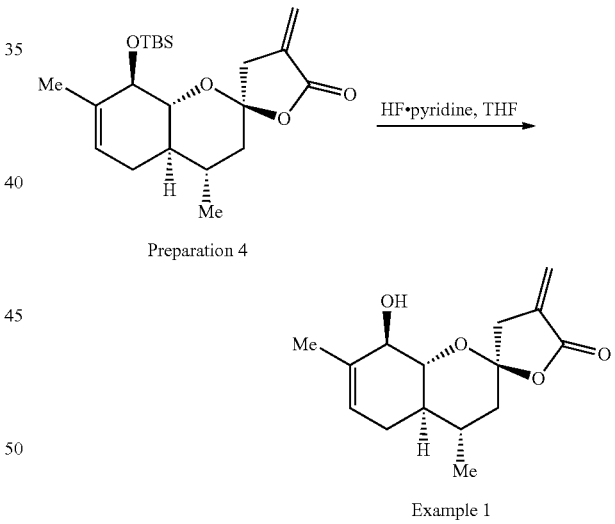

Preparation 4 (1.50 g, 3.96 mmol) was dissolved in THF (13.2 mL) and hydrogen fluoride pyridine (~70% hydrogen fluoride basis, 3.57 mL) was added dropwise at 0° C. The resulting solution was stirred for 16 h at room temperature, then cooled to 0° C. and saturated sodium bicarbonate solution (10 mL) was added dropwise, followed by ethyl acetate (10 mL). The aqueous phase was extracted three times with ethyl acetate (10 mL) and the organic phases were combined, washed with brine, dried over sodium sulfate, filtered and concentrated under reduced pressure. The resulting residue was purified by flash chromatography (hexanes:ethyl acetate 4:1 to 1:1) to yield Example 1 (1.01 g, 96%) as a white solid. $^1$H NMR (500 MHz, CDCl$_3$) δ 6.28

(dd, J=3.2, 2.5 Hz, 1H), 5.66 (t, J=2.5 Hz, 1H), 5.40 (dq, J=5.7, 2.0 Hz, 1H), 4.04 (dd, J=7.6, 3.7 Hz, 1H), 3.78 (dd, J=11.4, 8.0 Hz, 1H), 2.97 (dt, J=17.2, 2.3 Hz, 1H), 2.83 (dt, J=17.2, 2.9 Hz, 1H), 2.36-2.27 (m, 1H), 2.03 (d, J=3.5 Hz, 1H), 1.96-1.84 (m, 2H), 1.74 (s, 3H), 1.54-1.46 (m, 1H), 1.31-1.21 (m, 1H), 0.93 (d, J=6.4 Hz, 3H). $^{13}$C NMR (125 MHz, CDCl$_3$) δ 169.0, 134.3, 123.1, 122.2, 104.8, 79.39, 73.9, 42.6, 40.9, 40.7, 30.7, 28.8, 18.7, 18.5. IR (neat, cm$^{-1}$): 3477, 2969, 2954, 2887, 1760, 1215, 1131. HRMS (ESI): m/z=287.1260 calc. for C$_{15}$H$_{20}$O$_4$[M+Na]$^+$, found 287.1256.

Example 2: (2R,4S,4aR,8aR)-4,7-dimethyl-4'-methylene-3,3',4,4a,4',8a-hexahydro-5'H-spiro[chromene-2,2'-furan]-5',8(5H)-dione

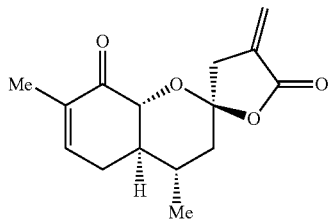 [SMILES: C=C1C[C@@]2(C[C@H](C)[C@H]3CC=C(C)C(=O)[C@@H]3O2)OC1=O]

Example 3: (2R,4S,4aR,8aR)-7-(hydroxymethyl)-4-methyl-4'-methylene-3,3',4,4a,4',8a-hexahydro-5'H-spiro[chromene-2,2'-furan]-5',8(5H)-dione

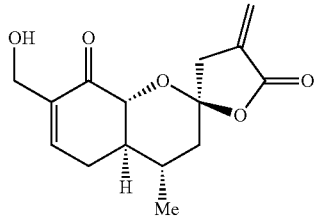 [SMILES: C=C1C[C@@]2(C[C@H](C)[C@H]3CC=C(CO)C(=O)[C@@H]3O2)OC1=O]

The synthesis of Example 2 and Example 3 is illustrated with Scheme 6:

Scheme 6: Synthesis of Example 2, Example 3, and Example 3'

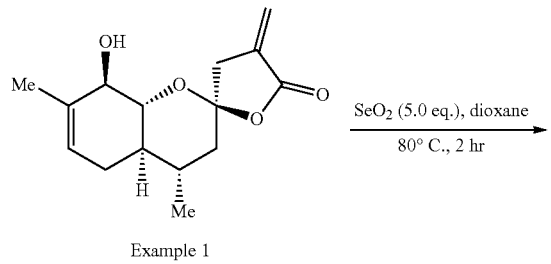

Example 1

SeO$_2$ (5.0 eq.), dioxane
80° C., 2 hr

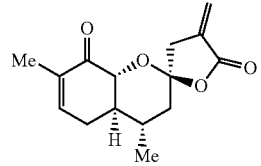

Example 2 (56%)

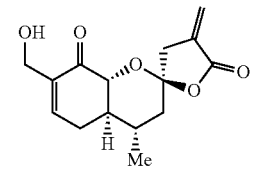

Example 3 (6%)

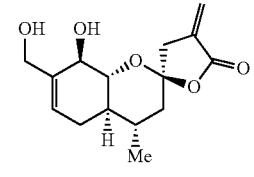

Example 3' (22%)

A solution of Example 1 (63 mg, 0.239 mmol) and selenium dioxide (132 mg, 1.19 mmol) in dioxane (4.0 mL) was stirred in a sealed vial at 80° C. for 2 h. After cooling to room temperature, the reaction mixture was filtered through Celite and concentrated under reduced pressure. The resulting residue was purified by flash chromatography (ethyl acetate to hexanes 2:1 to separate Example 2 from Example 3 and Example 3', followed by methylene chloride: methanol 95:5 to separate 30 from 31) to yield Example 2 as a white solid (35 mg, 56%), Example 3 as a white solid (4 mg, 6%), and Example 3' as a white solid (15 mg, 22%). Example 2: $^1$H NMR (500 MHz, CDCl$_3$) δ 6.66-6.60 (m, 1H), 6.27 (ddd, J=5.1, 3.2, 1.6 Hz, 1H), 5.68 (t, J=2.5 Hz, 1H), 4.40 (d, J=12.7 Hz, 1H), 3.18 (dt, J=17.4, 2.3 Hz, 1H), 2.83 (dt, J=17.4, 3.0 Hz, 1H), 2.66 (dtt, J=18.7, 4.7, 1.4 Hz, 1H), 2.16-2.05 (m, 2H), 1.93 (dd, J=13.8, 3.9 Hz, 1H), 1.78 (s, 3H), 1.70 (ddt, J=12.8, 10.7, 5.3 Hz, 1H), 1.52 (dd, J=13.8, 7.9 Hz, 1H), 0.98 (d, J=6.5 Hz, 3H.)$^{13}$C NMR (125 MHz, CDCl$_3$) δ 195.4, 168.9, 142.4, 135.0, 133.8, 123.7, 104.9, 77.7, 44.3, 42.1, 40.5, 31.2, 29.2, 18.2, 15.8. IR (neat, cm$^{-1}$) 2924, 1768, 1690, 1227, 1123. m/z=263.1283 calc. for C$_{15}$H$_{18}$O$_4$[M+H]+, found 263.1277. IR (neat, cm$^{-1}$): 2924, 1768, 1690, 1227, 1013. HRMS (ESI): m/z=263.1283 calc. for C$_{15}$H$_{18}$O$_4$[M+H]+, found 263.1283. Example 3: $^1$H NMR (500 MHz, CDCl$_3$) δ 6.89-6.85 (m, 1H), 6.30 (dd, J=3.2, 2.4 Hz, 1H), 5.70 (dd, J=2.8, 2.1 Hz, 1H), 4.46 (d, J=12.8 Hz, 1H), 4.31 (d, J=13.2 Hz, 1H), 4.22 (dd, J=13.6, 5.5 Hz, 1H), 3.17 (dt, J=17.4, 2.3 Hz, 1H), 2.84 (dt, J=17.4, 3.0 Hz, 1H), 2.77 (dddt, J=19.0, 5.8, 4.8, 1.0 Hz, 1H), 2.30 (t, J=6.6 Hz, 1H), 2.23-2.10 (m, 2H), 1.96 (dd, J=13.8, 3.9 Hz, 1H), 1.80-1.70 (m, 1H), 1.55 (dd, J=13.8, 12.5 Hz, 1H), 1.00 (d, J=6.6 Hz, 3H). $^{13}$C NMR (125 MHz, CDCl$_3$) δ 195.9, 168.8, 144.0, 137.6, 133.6, 123.9, 104.8, 77.51, 61.6, 44.1, 42.1, 40.4, 31.2, 29.1, 18.2. IR (neat, cm$^{-1}$): 3379, 2923, 2853, 1769, 1561, 1412, 1110. HRMS (ESI): m/z=279.1232 calc. for C$_{15}$H$_{18}$O$_4$[M+H]+, found 279.1217. Example 3': $^1$H NMR (500 MHz, CDCl$_3$) δ 6.29-6.28 (m, 1H), 5.68-5.66 (m, 2H), 4.34-4.32 (m, 1H), 4.17 (s, 2H), 3.84 (dd, J=11.4, 8.0 Hz, 1H), 2.99-2.94 (dt, J=15.0, 2.3 Hz, 1H), 2.86-2.80 (dt, J=17.2, 3.0 Hz, 1H), 2.41 (dt, J=18.0, 5.4

Hz, 1H), 1.95 (m, 1H), 1.92 (m, 1H), 1.81 (m, 1H), 1.56-1.48 (m, 1H), 1.32-1.22 (m, 1H), 0.94 (d, J=6.4 Hz, 3H). $^{13}$C NMR (125 MHz, CDCl$_3$) δ 168.9, 136.6, 134.1, 124.8, 123.1, 104.6, 78.7, 73.0, 64.8, 42.4, 40.7, 40.1, 30.5, 28.6, 18.4. IR (neat, cm$^{-1}$): 3420, 2923, 1764, 1216. HRMS (ESI) m/z=303.1203 calc. for C$_{15}$H$_{20}$O$_5$Na [M+Na]+=303.1203, found 303.1203.

Example 4: (2R,4S,4aR,8aR)-7-(azidomethyl)-4-methyl-4'-methylene-3,3',4,4a,4',8a-hexahydro-5'H-spiro[chromene-2,2'-furan]-5',8(5H)-dione

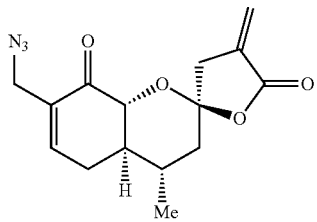 [SMILES: C=C1C[C@@]2(C[C@H](C)[C@H]3CC=C(CN=[N+]=[N-])C(=O)[C@@H]3O2)OC1=O]

The synthesis of Example 4 is illustrated with Scheme 7

Scheme 7: Synthesis of Example 4

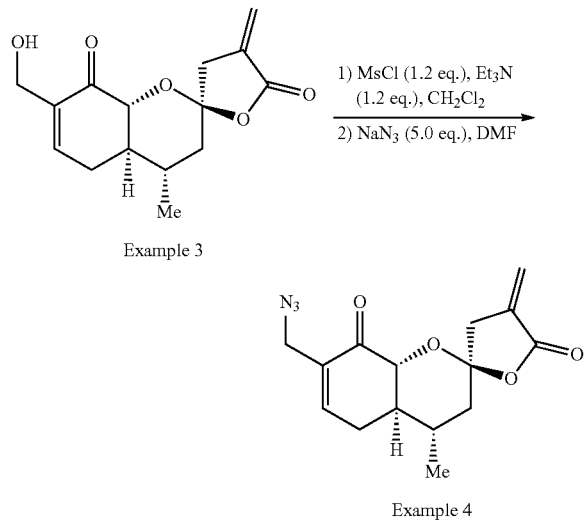

To a solution of Example 3 (10 mg, 0.036 mmol) in CH$_2$C$_{12}$ (0.36 mL) was added Et$_3$N (6 μL, 0.0432 mmol). The resulting solution was cooled to 0° C. and methanesulfonyl chloride (2.5 μL, 0.0432 mmol) was added. After stirring for 1 h, brine (1 mL) and CH$_2$Cl$_2$ (1 mL) were added. The aqueous phase was extracted with CH$_2$Cl$_2$ (3×1 mL) and the combined organic layers were dried over sodium sulfate, filtered and concentrated under reduced pressure. The resulting crude residue was dissolved in DMF (0.36 mL) and sodium azide (11.7 mg, 0.18 mmol) was added. The reaction vessel was covered with aluminium foil and the solution stirred for 18 h. Water (1 mL) and ethyl acetate (1 mL) were added and the aqueous phase extracted with ethyl acetate (3×1 mL.) The combined organic phases were washed with brine (2 mL), dried over sodium sulfate, filtered and concentrated under reduced pressure. The crude residue was purified by flash chromatography (methylene chloride: ethyl acetate 50:1 to 20:1 to 10:1) to yield Example 4 as a colorless oil (3.8 mg, 35%). $^1$H NMR (500 MHz, CDCl$_3$) δ 6.91 (d, J=6.2 Hz, 1H), 6.30 (t, J=2.9 Hz, 1H), 5.70 (t, J=2.5 Hz, 1H), 4.47 (d, J=12.8 Hz, 1H), 3.99 (q, J=14.5 Hz, 2H), 3.18 (dt, J=17.4, 2.3 Hz, 1H), 2.89-2.76 (m, 2H), 2.27-2.11 (m, 2H), 1.96 (dd, J=13.8, 3.9 Hz, 1H), 1.80-1.69 (m, 1H), 1.01 (d, J=6.5 Hz, 3H). $^{13}$C NMR (125 MHz, CDCl$_3$) δ 193.9, 168.8, 145.2, 133.6, 123.9, 104.7, 77.4, 49.4, 44.0, 42.0, 40.4, 31.3, 29.2, 18.2. IR (neat, cm$^{-1}$): 2924, 2853, 2105, 1770, 1634, 1261, 1014. HRMS (ESI): m/z=326.1117 calc. for C$_{15}$H$_{19}$N$_3$O$_4$[M+Na]$^+$, found 326.1110.

Target Identification Procedure

Materials and General Methods

DMEM/High glucose media with GlutaMAX and sodium pyruvate, phosphate buffered saline (PBS), MEM Non-Essential Amino Acids, Penicillin Streptomycin (Pen/Strep), Trypsin-EDTA and OptiMEM were obtained from Life Technologies. Protein concentration was determined using the Bradford assay (Bio-Rad). Cloning of POLE3-GFP was done using the Gateway technology (Thermo Fisher Scientific). Plasmids were prepared using the QIAprep Spin Miniprep Kit (Qiagen). For all PCR reactions, Q5® High-Fidelity DNA Polymerase (New England BioLabs Inc) was used as recommended by the manufacturer. PCR cleanup was performed using agarose gel electrophoresis with subsequent cutting of amplified bands using QIAquick Gel Extraction Kit (Qiagen) following the protocol of the producer. For the BP and the LR reactions the Gateway® BP Clonase® Enzyme Mix and the Gateway® LR Clonase® Enzyme mix (Thermo Fisher Scientific) were used according to the protocol of the manufacturer. siRNA for POLE3 was purchased from Dharmacon (ON-TARGETplus Human POLE3 SMARTpool).

Cell Culture and Preparation of Lysates

MDA-MB-231, HeLa and 293T cells were maintained in DMEM media. All media were supplemented with 10% fetal calf serum (FCS), non-essential amino acids and penicillin/streptomycin. Cells were grown at 37° C. under 5% CO$_2$ atmosphere. Cells were allowed to grow to confluence and were harvested by scraping, centrifuged at 1'500×g for five min. at 4° C. and resuspended in PBS. Cells were lysed by sonication to form cell lysates and protein concentration was determined using the Bradford assay.

Preparation of Proteomes for SDS-PAGE Experiments

MDA-MB-231 lysate (2 mg/mL, 25 μL) was treated with indicated concentrations of azide probes (Example 4) (1 μL of 25× stock in DMSO) for one hour at r.t. Click chemistry was initiated by the addition of TAMRA alkyne (Sigma-Aldrich, 30 μM, 25× stock in DMSO), tris(2-carboxyethyl) phosphine hydrochloride (TCEP, Alfa Aesar, 1 mM, fresh 50× stock in water), tris[(1-benzyl-1H-1,2,3-triazol-4-yl)methyl]amine (TBTA, Sigma-Aldrich, 100 μM, 16× stock in DMSO:tBuOH 1:4), and copper(II) sulfate (1 mM, 50× stock in water) to the lysate and incubated in the dark for one hour at r.t. SDS-PAGE reducing loading buffer (4×) was added and proteins were separated using a 10% SDS-PAGE gel. Gels were visualized using an Azure Biosystems Sapphire Biomolecular Imager, then stained using Coomassie. Images were quantified with ImageJ (V1.51).

Gel-Based In Vitro JW-RF-001 Competition of Labeling with Example 4

MDA-MB-231 lysate (2 mg/mL, 25 μL) was treated with either 3 mM JW-RF-001 (1 μL of 25× stock in DMSO) or DMSO for one hour at r.t. Subsequently, lysate was incubated with 30 μM Example 4 (1 μL of 25× stock in DMSO) for one hour at r.t. Click chemistry, reducing SDS-PAGE and visualization were performed as described above. The study showed that Example 4 binded to cysteines, as pretreatment of the lysates with the cysteine-reactive reagent JW-RF-001 completely abolished the labeling.

Cloning and Site-Directed Mutagenesis

The POLE3-WT gene was amplified from a cDNA library derived from HeLa cells and flanked with Attb-sites using the following primer: forward 5'-GGG GAC AAG TTT GTA CAA AAA AGC AGG CTC CAT GGC GGA GAG GCC C-3' (SEQ ID NO:1) and reverse 5'-GGG GAC CAC TTT GTA CAA GAA AGC TGG GTC GTT GTC TAC TTC TTC CTC TTC ATT CT-3' (SEQ ID NO:2). The PCR reaction was cleaned up and the PCR product recombined into the pDONR 221. pENTR was used for transferring the POLE3-WT gene into the pcDNA 6.2 N-EmGFP-DEST via the LR reaction to merge the emGFP gene to the 3' of the gene to obtain POLE3-GFP-pEXP. This pEXP was used for PCR based site directed mutagenesis to generate the mutated pEXP vector POLE3-051S-GFP-pEXP (forward primer: 5'-TCC TCT GCT AAC AAC TTT GCA ATG AAA GGA-3'(SEQ ID NO:3); reverse primer: 5'-AGC AGA GGA TGT GGC GTA CAG CAC GAA GAC-3' (SEQ ID NO:4)). Afterwards the PCR reaction was incubated with DpnI (New England BioLabs Inc, 37° C., 12 hours followed by 80° C. for 20 min.) to degrade POLE3-WT-GFP-pEXP. The pENTR and pEXP plasmids were propagated via transformation into *E. coli* DH5α using heat shock.

Transfection, Gel-Based In Vitro Labeling Experiments Using Probe Example 4 and Western Blots 293T cells in a 3.5 cm Petri dish were transfected with POLE3-WT-GFP-pEXP or POLE3-051S-GFP-pEXP using PEI-MAX. After 24 hours, lysates were prepared as described above. Proteins (1 mg/mL, 25 µL) were incubated with indicated compounds at indicated concentrations (25× stock in DMSO) for three hours at 37° C. Subsequently, 30 µM Example 4 (25× stock in DMSO) was added for one hour at r.t. Click chemistry, reducing SDS-PAGE and visualization were performed as described above. Proteins were transferred to a PVDF membrane using a Trans-Blot Turbo transfer system (Bio-Rad). Membrane was blocked with 3% BSA in Tris-Buffered Saline with 0.1% Tween 20 (TBST) for one hour at r.t. Mouse monoclonal antibody against GFP (Roche, 1/1000 in 3% BSA in TBST) was added and incubated overnight at 4° C. Membrane was washed three times for five min. with TBST and incubated with anti-mouse Alexa Fluor 647 (Jackson ImmunoResearch Inc., 1/500 in 3% BSA in TBST) for one hour at r.t. Membrane was washed four times for five min. with TBST and visualized with an Azure Biosystems Sapphire Biomolecular Imager.

Gel-Based Determination of Kinetic Parameters $K_I$ and $K_{inact}$

WT POLES-GFP was overexpressed in 293T cells as described above and lysate was treated with indicated concentrations of Example 2 (1 µL of 25× stock in DMSO) for 1.5, 2, 2.5, 3, 3.5 or 4 hours at 37° C. Samples were then treated with 30 µM Example 4 (1 µL of 25× stock in DMSO) for one hour at r.t. Click chemistry, reducing SDS-PAGE and visualization were performed as described above. Images were quantified using ImageJ and the kinetic parameters were determined using GraphPad Prism (V7.02).). The application of Kitz and Wilson method (see Kitz, R.; Wilson, I. B. *J. Biol. Chem.* 1962, 237, 3245-3249) provided the Example 2 POLE3-GFP binding constants $K_i$ (56.9 µM) and $k_{inact}$ (0.27 min$^{-1}$), respectively.

To understand whether binding of Example 2 to $C_{51}$ of POLE3 is productive and leads to the loss of function of this protein, POLE3 was knocked down in HeLa cells using siRNA and compared by global proteomics the protein expression profile in these cells versus cells treated with compound Example 2 or DMSO as control. There are 224 overexpressed and 216 downregulated proteins found in POLE3 KD cells versus cells treated with DMSO. Moreover, there is a significant overlap in up- and downregulated proteins between the POLE3 KD cells and the cells after 6 h treatment with Example 2. It indicated that binding by Example 2 indeed leads to the loss of function of POLE3. It was found several proteins involved in DNA repair that were upregulated in both POLE3 KD and Example 2-treated cells, such as DNA ligase 3, GEMIN2, PEA15 and GIT2. Possibly as a compensatory effect, we also observed fourfold upregulation of POLE, another subunit of DNA polymerase E. These results suggest that POLE3 may indeed be involved in endogenous DNA repair pathways, although clearly deeper biological insight is required to decipher the mechanistic role of POLE3 in these critical processes.

Visualization of DNA Double Strand Breaks for Microscopy (γH2AX)

HeLa cells were seeded (250'000 cells/mL) in a 6-well plate and reverse transfected with scrambled siRNA or POLE3 siRNA using RNAiMAX for two days. Cells were trypsinizned, seeded (150'000 cells/mL) in a 24-well plate containing a coverslip and left overnight to attach and grow. Cells were incubated for 6 hours in media without FCS with either DMSO (0.2% final), 30 µM etoposide, 30 µM Example 2 or 30 µM etoposide together with 30 µM Example 2. Cells were washed one time with PBS and fixed with methanol at 20° C. for 10 min. Cells were washed again two times with PBS and coverslip was transferred to a wet box. Blocking was performed with a 5% bovine serum albumin (BSA) solution in PBS for 30 min. Cells were washed one time with PBS 0.1% BSA and rabbit antibody directed against H2AX pSer$^{139}$ (Sigma Aldrich H5912, 1/250 in PBS 0.1% BSA) was added and incubated for one hour at r.t. Cells were washed three times with PBS 0.1% BSA and incubated for one hour with anti-rabbit IgG Alexa Fluor 488 (Jackson, 1/200 in PBS 0.1% BSA). Cells were washed three times with PBS 0.1% BSA, one time with PBS, one time with water and then mounted on a slide with ProLong Gold antifade mountant with DAPI (Life Technologies). Cells were visualized with an LSM 700 confocal microscope (Zeiss).

Due to its potential involvement in DNA repair pathways, studies were carried out to investigate the effect of POLE3 knockdown or inactivation by Example 2 in combination with a DNA damaging agent such as etoposide. Etoposide is a clinically applied drug to treat numerous types of cancer. It forms a ternary complex with DNA and topoisomerase II to eventually cause DNA strand breakage. Briefly, HeLa cells were treated or not with POLE3 siRNA and then subsequently exposed to treatment by 30 µM etoposide, 30 µM Example 2, or 30 µM etoposide combined with 30 µM Example 2. Induced DNA damage was measured by confocal microscopy using γH2AX staining as marker. Treatment with Example 2 alone did not lead to an increase in γH2AX signal intensity. However, intriguingly, significantly stronger γH2AX signal was observed in cells treated with both etoposide and Example 2 versus etoposide only-treated cells. Likewise, POLE3 KD cells did not show increased DNA damage, but adding etoposide again caused increased γH2AX signal in comparison to the etoposide-treated wild type cells. These results demonstrate that targeting POLE3 with small molecules may indeed be a novel strategy for chemosensitization to DNA damaging drugs in cancer.

Global Proteomics Profiling Using LC-MS/NIS

Knockdown of POLE3 was achieved using RNAiMAx (Invitrogen) and POLE3 siRNA (Dharmacon) via reverse transfection according to the manual of the manufacturer. Briefly, 9 μL of 20 μM siRNA was mixed with 9 μL of RNAiMax reagent in 500 μL OptiMEM and incubated for 20 min. at r.t. HeLa cells (250'000 cells/mL) were seeded in a 6-well plate on top and incubated for 48 hours at 37° C. Cells were washed twice with PBS and treated with DMSO (0.1% final) or 30 μM Example 2 for 6 hours at 37° C. Cells were washed with PBS and lysate was prepared as mentioned above. To 25 μL lysate (1 mg/mL) in PBS, Urea was added to 6 M final concentration and incubated with 10 mM TCEP for 20 min. at r.t. under rotation. For alkylation, 25 mM IAA was added and incubated for 20 min. at r.t. under rotation. Solution was diluted to 2 M Urea with 50 mM $NH_4HCO_3$ and 1 mM $CaCl_2$, then 0.5 μg trypsin (Thermo Scientific) was added. Tryptic digestion was performed overnight at 37° C. Peptides were desalted over a self-packed C18 spin column and dried. Samples were analyzed by LC-MS/MS (see below) and the MS data was processed with MaxQuant (see below).

In Situ Competitive Experiment for Mass Spectrometry

MDA-MB-231 or HeLa cells were seeded in 14 cm Petri dishes and left to attach and grow until confluence. Cells were washed one time with PBS and treated with either DMSO or 30 μM Example 2 for 6 hours in media without FCS at 37° C. Lysate was prepared as described above. Lysate (2 mg/mL, 0.75 mL) was treated with 30 μM Example 4 (100× stock in DMSO) for one hour at r.t. and then subjected to click chemistry. Photocleavable (PC) biotin alkyne (Click Chemistry Tools, 60 μM, 50× stock in DMSO), tris(2-carboxyethyl)phosphine hydrochloride (TCEP) (1 mM, 50× fresh stock in water), tris[(1-benzyl-1H-1,2,3-triazol-4-yl)methyl]amine (TBTA) (100 μM, 16× stock in DMSO:tButanol 1:4), and copper(II) sulfate (1 mM, 50× stock in water) were added to the proteome and left to react for one hour at r.t. Protein was precipitated by adding MeOH (4 vol.), $CHCl_3$ (1 vol.) and water (3 vol.) to the reaction mixture and the turbid mixture was centrifuged for five min. at 20'000×g at 4° C. yielding a protein layer between the aqueous and organic layers. The protein layer was isolated, dried and solubilized in 2% SDS in PBS via sonication. Tube was centrifuged at 4'700×g for five min. and soluble fraction was transferred to a new tube. PBS was added to give a final SDS concentration of 0.2%. 160 μL of streptavidin agarose beads (ProteoChem) were added and the mixture was rotated for four hours at r.t. Beads were washed with 1% SDS in PBS (1×10 mL), PBS (3×10 mL), and water (3×10 mL). Beads were resuspended in 6 M urea in PBS (500 μL), reduced with 10 mM neutralized TCEP (20× fresh stock in water) for 30 min. at r.t., and alkylated with 25 mM iodoacetamide (400 mM fresh stock in water) for 30 min. at r.t. in the dark. Beads were pelleted by centrifugation (1'400×g, two min.) and resuspended in 150 μL of 2 M Urea, 1 mM $CaCl_2$ (100× stock in water) and trypsin (Thermo Scientific, 1.5 μL of 0.5 μg/μL) in 50 mM $NH_4HCO_3$. The digestion was performed for 6 hours at 37° C. Samples were acidified to a final concentration of 5% acetic acid, desalted over a self-packed $C_{18}$ spin column and dried. Samples were analyzed by LC-MS/MS (see below) and the MS data was processed with MaxQuant (see below).

LC-MS/NIS Analysis

Peptides were resuspended in water with 0.1% formic acid (FA) and analyzed using EASY-nLC 1200 nano-UHPLC coupled to Q Exactive HF-X Quadrupole-Orbitrap mass spectrometer (Thermo Scientific). The chromatography column consisted of a 30 cm long, 75 μm i.d. microcapillary capped by a 5 μm tip and packed with ReproSil-Pur 120 C18-AQ 2.4 μm beads (Dr. Maisch GmbH). LC solvents were 0.1% FA in $H_2O$ (Buffer A) and 0.1% FA in 90% MeCN: 10% $H_2O$ (Buffer B). Peptides were eluted into the mass spectrometer at a flow rate of 300 nL/min. over a 240 min. linear gradient (5-35% Buffer B) at 65° C. Data was acquired in data-dependent mode (top-20, NCE 28, R=7'500) after full MS scan (R=60'000, m/z 400-1'300). Dynamic exclusion was set to 10 s, peptide match to prefer and isotope exclusion was enabled.

MaxQuant Analysis

The MS data was analyzed with MaxQuant (V1.6.1.0) and searched against the human proteome (Uniprot) and a common list of contaminants (included in MaxQuant). The first peptide search tolerance was set at 20 ppm, 10 ppm was used for the main peptide search and fragment mass tolerance was set to 0.02 Da. The false discovery rate for peptides, proteins and sites identification was set to 1%. The minimum peptide length was set to 6 amino acids and peptide re-quantification, label-free quantification (MaxLFQ) and "match between runs" were enabled. The minimal number of peptides per protein was set to two. Methionine oxidation was searched as a variable modification and carbamidomethylation of cysteines was searched as a fixed modification.

Protein Tyrosine Phosphatase Inhibition Evaluation

PTP Inhibition Study. *Abies* sesquiterpenoids and their analogs were evaluated for their ability to inhibit the reaction catalyzed by PTP1B and SHP2 using p-nitrophenyl phosphatae (pNPP) as a substrate at pH 7 and 25° C. The reaction was started in a 384 plate, by the addition of 25 μL of the enzyme (40 nM stock concentration or 17.7 mg/ml) to 25 μL of reaction mixture containing 6 mM (2× the $K_m$ value) of pNPP and various concentrations of the inhibitor (added by Echo, volume between 2.5 to 500 nl), in a buffer containing 50 mM 3,3-dimethylglutarate, 1 mM EDTA, and ionic strength of 150 mM adjusted with NaCl. the initial rate at a series of pNPP concentrations was measured by following the production of p-nitrophenol. The reaction was quenched after 3 (PTP1B) or 15 (SHP2) min by the addition of 25 μl of 5N NaOH. The absorbance at 405 nm was detected by a Spectra MAX 384 PLUS microplate spectrophotometer (Molecular Devices). $IC_{50}$ values were calculated by fitting the absorbance at 405 nm versus inhibitor concentration to the following equation:

$$A_1/A_0 = IC_{50}/(IC_{50}+[I])$$

wherein $A_1$ is the absorbance at 405 nm of the sample in the presence of inhibitor; $A_0$ is the absorbance at 405 nm in the absence of inhibitor; and [I] is the concentration of the inhibitor.

Kinetic Characterization of SHP2 Inactivation by Example 3'. PTP inactivation by the vinyl sulfonates and sulfones was studied at 25° C. in a pH 7 buffer containing 50 mM sodium succinate, 1 mM EDTA, and ionic strength of 150 mM adjusted with NaCl. The assay was performed in a 96 well plate, starting with preparation of a series of inactivator solutions at various concentrations in one column. At appropriate time intervals, aliquots of 4 µl were removed from the reaction and added into a 200 µl solution containing 20 mM pNPP at 25° C. in the above buffer. The remaining PTP activity was measured using procedures described above. The kinetic parameters of the inactivation reaction were obtained by fitting the data to the following equations:

$$\frac{A_t}{A_0} = \frac{A_\infty}{A_0} - \left(\frac{A_0 - A_\infty}{A_0}\right) e^{-k_{obs} \cdot t}$$

Example 2, Example 3, and Example 3' provided SHP2 $IC_{50}$ values of 44.9±9.6 µM, 33.3±0.9 µM, and 3.3±0.1 respectively. Example 2, Example 3, and Example 3' also provided 10-fold preference for SHP2 over PTP1B. Therefore, the exemplified compounds in the present disclosure may be used as SHP2 inhibitors for a variety of cancer treatments. See Frankson, R.; Yu, Z.-H.; Bai, Y.; Li, Q.; Zhang, R.-Y.; Zhang, Z.-Y. *Cancer Res.* 2017, 77, 5701-5705.

Those skilled in the art will recognize that numerous modifications can be made to the specific implementations described above. The implementations should not be limited to the particular limitations described. Other implementations may be possible.

We claim:

1. A method of inhibiting; Src homology domain containing phosphatase 2 (SHP2) in a patient with cancer, which method comprises administering to the patient a compound of:

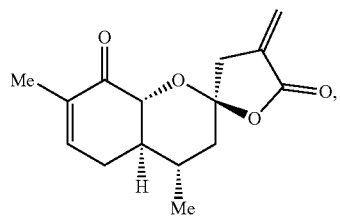

Formula I

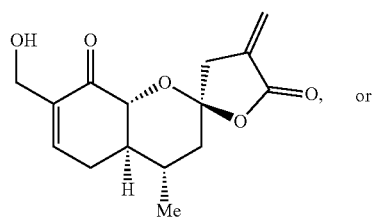

Formula II or

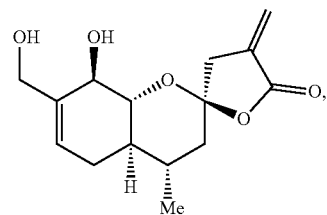

Formula III or any stereoisomer of the foregoing or a combination thereof, whereupon SHP2 in the patient with cancer is inhibited.

2. The method of claim 1, wherein the compound is Formula III or any stereoisomer thereof.

3. The method of claim 1, wherein the patient is being treated with a DNA damaging drug.

4. The method of claim 3, wherein the DNA damaging drug is ectoposide.

5. The method of claim 2, wherein the patient is being treated with a DNA damaging drug.

6. The method of claim 5, wherein the DNA damaging drug is ectoposide.

* * * * *

SEQUENCE LISTING

<160> NUMBER OF SEQ ID NOS: 4

<210> SEQ ID NO 1
<211> LENGTH: 46
<212> TYPE: DNA
<213> ORGANISM: artificial
<220> FEATURE:
<223> OTHER INFORMATION: POLE3-WT gene forward

<400> SEQUENCE: 1
ggggacaagt ttgtacaaaa aagcaggctc catggcggag aggccc            46

<210> SEQ ID NO 2
<211> LENGTH: 56
<212> TYPE: DNA
<213> ORGANISM: artificial
<220> FEATURE:
<223> OTHER INFORMATION: POLE3_WT gene reverse

<400> SEQUENCE: 2
ggggaccact ttgtacaaga aagctgggtc gttgtctact tcttcctctt cattct    56

<210> SEQ ID NO 3
<211> LENGTH: 30
<212> TYPE: DNA
<213> ORGANISM: artificial
<220> FEATURE:
<223> OTHER INFORMATION: POLE3-C51S-GFP-pEXP forward

<400> SEQUENCE: 3
tcctctgcta acaactttgc aatgaaagga                              30

<210> SEQ ID NO 4
<211> LENGTH: 30
<212> TYPE: DNA
<213> ORGANISM: artificial
<220> FEATURE:
<223> OTHER INFORMATION: POLE3-C51S-GFP-pEXP reverse

<400> SEQUENCE: 4
agcagaggat gtggcgtaca gcacgaagac                              30